(12) United States Patent
Takahata

(10) Patent No.: US 7,034,058 B2
(45) Date of Patent: Apr. 25, 2006

(54) ANTI-TUMOR PHARMACEUTICAL COMPOSITION COMPRISING N-VANILLYL FATTY ACID AMIDE

(75) Inventor: Kyoya Takahata, Okayama (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 10/634,641

(22) Filed: Aug. 4, 2003

(65) Prior Publication Data

US 2004/0110844 A1    Jun. 10, 2004

(30) Foreign Application Priority Data

Dec. 5, 2002    (JP) .............................. 2002-353649

(51) Int. Cl.
*A61K 31/16* (2006.01)
(52) U.S. Cl. ........................................ 514/625; 554/65
(58) Field of Classification Search ............... 514/625; 554/65
See application file for complete search history.

(56) References Cited

U.S. PATENT DOCUMENTS

| 4,898,887 | A | * | 2/1990 | Janusz et al. ............... 514/642 |
|---|---|---|---|---|
| 5,221,692 | A | * | 6/1993 | Chen .......................... 514/625 |
| 6,022,718 | A | | 2/2000 | Iwai et al. |
| 2004/0122089 | A1 | * | 6/2004 | Martin et al. ............... 514/509 |

FOREIGN PATENT DOCUMENTS

WO    WO 00/16756    3/2000

OTHER PUBLICATIONS

Janusz et al., J. Med. Chem. (1993), 36, pp. 2595-2604.*
HCAPLUS, DN 141:99178, Jin et al., Nippon Shokuhin Kagaku Gakkaishi, 9(2), 50-53 (2002) abstract only.*
HCAPLUS, DN 139:142982, Takahata et al., New Food Industry, 44(10), 6-12 (2002), abstract only.*
Morre et al. "Capsaicin inhibits preferentially the NADH oxidase and growth of transformed cells in culture" *Proc. Nat;. Acad. Sci.USA* vol. 92, pp. 1831-1835, Mar. 1995.
Takahata et al. "Growth Inhibition of capsaicin on hela cells is not mediated b intracellular calcium mobilization" *Life Sciences*, vol. 64, No. 13, pp. PL 165-171 (1999).
Szallasi et al. "Resiniferatoxin and its analogs provide novel insights into the pharmacology of the vanilloid (capsaicin) receptor" *LifeSciences* vol. 47, pp. 1399-1408 (1990).

Morre et al. "Capsaicin inhibits plasma membrane NADH oxidase and growth of human and mouse melanoma lines" *European Journal of Cancer*, vol. 32A, No. 11, pp. 1995-2003, (1996).
Melck, et al., "Suppression of nerve Growth Factor Trk receptors and prolactin receptors by endocannabinoids leads to inhibition of human breast and prostate cancer cell proliferation," Endocrinology, vol. 141, No. 1, pp. 118-126 (2000) (Document No. XP-002272763).
Melck, et al., "Unsaturated long-chain N-Acyl-vanillyl-amindes (N-AVAMs): vanilloid receptor ligands that inhibit anandamide-facilitated transport and bind to SB1 cannabinoid receptors," Biochemical and Biophysical Research Communications, Academic Press Inc., vol. 9, No. 13, pp. 275-284 (Document No. XP-000892119).
Jacobsson, et al., "Inhibition of rat c6 glioma cell proliferation by endogenous and synthetic cannabinoids. Relative involvement of cannabinoid and vanilloid receptors," Journal of Pharmacology and Experimental Therapeutics, American Society for Pharmacology and Experimental Therapeutics, vol. 299,No. 3, pp. 951-959 (2001) (Document No. XP-001120403).

(Continued)

*Primary Examiner*—Christopher S. F. Low
*Assistant Examiner*—C. Delacroix-Muirheid
(74) *Attorney, Agent, or Firm*—Carol L. Francis; Bozicevic, Field & Francis LLP

(57) ABSTRACT

The present invention provides an anti-tumor pharmaceutical composition having a high anti-tumor effect with low side-effects. The anti-tumor pharmaceutical composition comprises a N-vanillyl fatty acid amide of formula (1):

(1)

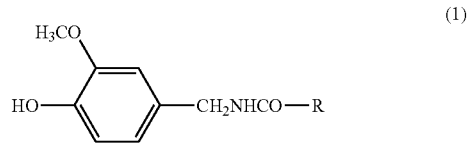

wherein —CO—R group represents a saturated or unsaturated fatty acid residue containing from 14 to 32 carbon atoms. Accordingly the invention provides an anti-tumor pharmaceutical composition comprising a N-vanillyl fatty acid amide which relates to capsaicin wherein the composition has a low side-effect and a high anti-tumor effect, in particular an anti-melanoma effect and an anti-leukemia cell effect; and is very low pungent, stimulatory and preinflammatory effect.

9 Claims, 6 Drawing Sheets

OTHER PUBLICATIONS

De Petrovellis, et al. "Endocannabinoids and fatty acid amides in cancer, inflammation and related disorders," Chemistry and Physics of Lipids, vol. 108, pp. 191-209 (2000) (Document No. XP-002941399).

Di Marzo, et al., "Highly selective $CB_1$ cannabinoid receptor ligands and novel $CB_1$/ $VR_1$ vanilloid receptor "hybrid" ligands," Biochemical and Biophysical Research Communications, vol. 281, No. 2, pp. 444-451 (2001) (Document No. XP-002272764).

Takahata, et al., "Inducting effect of cancer cell apoptosis by docosahexaenoic acid (DHA) derivatives (Dohevanil) of a hot ingredient of red pepper, capsaisin," New Food Industry, 44(10), 6-10, (2002) (Document No. XP-009026691) and English Translation Provided.

Keisuke, et al., "Homovanillic acid derivative, capsaisin, induces apoptosis of myeloid leukemic cel via a p53-dependent pathway in vitro and in vivo," Database Accession No. PREV 200300368073, Blood, vol. 100, No. 11 (Nov. 16, 2002) pg. Abstract No. 4589, 44th Annual Meeting of the American Society of Hematology: Philadelphia PA (Dec. 6-10, 2002) (Document No. XP-0022722766).

Patel, et al., "Capsaicin regulates vascular endothelial cell growth factor expression by modulation of hypoxia inducing factor-$1\alpha$ in human malignant melanoma cells," J. Cancer Res Clin Oncol, vol. 128, pp. 461-468 (2002) (Document No. XP-002272765).

Di Marzo, et al., "Interactions between synthetic vanilloids and the endogenous cannabinoid system," FEBS Letters, Elsevier Science Publishers, Amsterdam, NL., vol. 436,No. 3, pp. 449-454 (1998) (Document No. XP-004258472).

Sherwin, et al., "Human melanoma cells have both nerve growth factor and nerve growth factor-specific receptors on their cell surfaces," Proc. Natl. Acad Sci. USA, vol. 76, No. 3, pp. 1288-1292 (1997) (Document No. XP-009026810).

De Cabo, et al., "Inhibition of growth and metastasis of B-16 mouse melanoma cells inhibited by capsaisin," Molecular Biology of the cell, vol. 7, no. Suppl, p. 172A (1996) (Document No. XP-009026860).

* cited by examiner

Effects of Capsaicin and Dohevanil to growth of HeLa cells

Effects of Capsaicin and Dohevanil to growth of NIH/3T3 cells

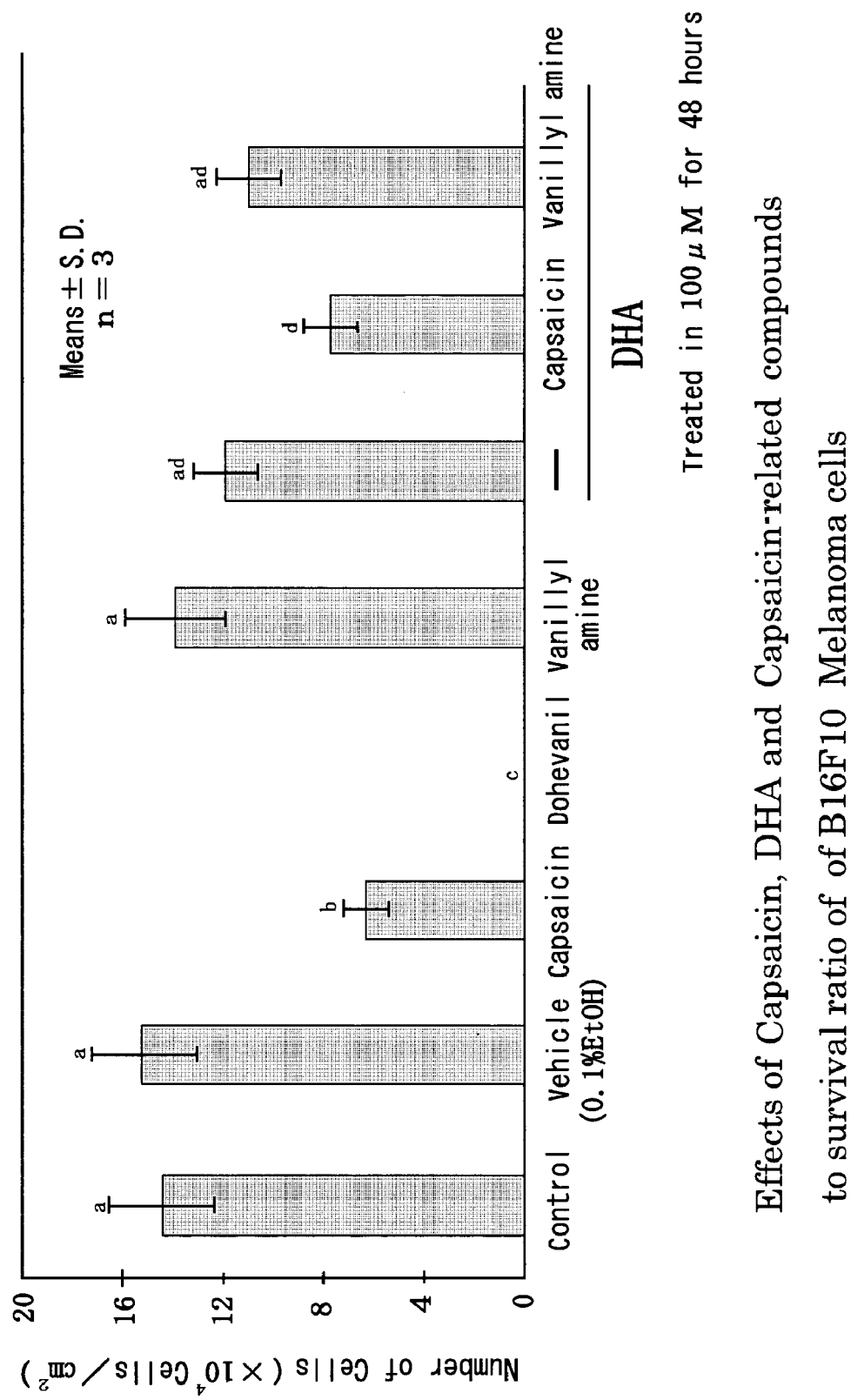

ANTI-TUMOR PHARMACEUTICAL COMPOSITION COMPRISING N-VANILLYL FATTY ACID AMIDE

FIELD OF THE INVENTION

The present invention relates to an anti-tumor pharmaceutical composition. In particular, the present invention relates to an anti-tumor pharmaceutical composition having an antiproliferative effect on melanoma cells and leukemia cells.

BACKGROUND OF THE INVENTION

Recently, the following are done for the cancer therapy: surgical therapy, radiotherapy, and chemotherapy. The chemotherapy is conventionally done by administering to the patients agents which directly act on tumor cells and then kill them. Lots of anti-tumor agents which can be used in the chemotherapy have been known. Since the agents used in the conventional chemotherapy not only kill the tumor cells but act on the normal cells, it has been the problem that the agents have very strong side effects, although they have an high treatment efficiency to the cancers.

It is known that capsaicin (8-methyl-N-vanillyl-6-nonenamide), which is a hot ingredient of red pepper widely used as a spice, has a strong hot taste and preferable effects to a living organism such as appetitive promotion, vascular dilatation, vasoconstriction, enhancement of energy metabolism, and release promotion of biologically active peptides. Recently, the anti-tumor effects of capsaicin has been reported in addition to these preferable physiological effects (D. J. Morre et. al., Proc. Natl. Acad. Sci., 92, 1831–1835 (1995), and K. Takahata et. al, Life Science, 64, PL 165–171 (1999)). Namely, capsaicin has a proliferative inhibitory effect in a low concentration to Hela cell derived from a human (uterocervica cancer cell) and HL-60 cell (acute promyelocytic leukemia cell). However, although capsaicin induces apoptosis-like changes such as nuclear segmentation and agglutination to many survived cells, it has been found that capsaicin specifically acts on the tumor cells without any proliferative inhibitory effects to normal cells of human mammary gland epithelium and of liver and kidney of the rat (D. J. Morre et. al., Proc. Natl. Acad. Sci., 92, 1831–1835 (1995)). As a result, capsaicin has been expected to become an efficient anti-tumor agent with low side effects.

To the contrary, capsaicin is difficult to use as a pharmaceutical agent because of its hot taste, stimulus and inflammation induction, and its continuous administration is stressful to the patients.

SUMMARY OF THE INVENTION

An object of the present invention is to provide an anti-tumor pharmaceutical composition comprising capsaicin related-ingredient, the N-vanillyl fatty acid amide which causes low side effects with high anti-tumor effects like capsaicin and which is low in hot taste, stimulus and inflammation induction.

The inventor performed his study on the basis of the findings that the N-vanillyl fatty acid amide produced by substituting 8-methyl-6-nonene residue of capsaicin with an acyl group (—CO—R group) having 14 or more carbon atoms is low in the hot taste and stimulus, and that the vanillyl amine structure of the amide combines with a vaniloid receptor which is an intravital receptor necessary to cause physiological effects of capsaicin (A. Szallasi et. al., Life Sci., 47, 1399–1408 (1990)). As a result, the inventor found the capsaicin related-ingredient, certain N-vanillyl fatty acid amides which cause low side effects with high anti-tumor effects, in particular a high anti-melanoma effect and a high anti-leukemia cell effect and which are low in hot taste, stimulus and inflammation induction.

Accordingly, the present invention provides an anti-tumor pharmaceutical composition comprising a N-vanillyl fatty acid amide of formula (1):

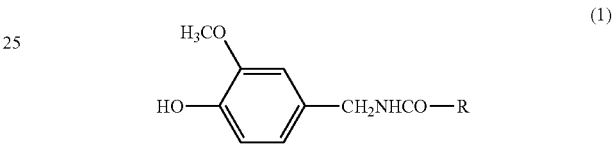

wherein —CO—R group represents a saturated or unsaturated fatty acid residue containing from 14 to 32 carbon atoms.

The present invention also provides an anti-melanoma pharmaceutical composition comprising a N-vanillyl fatty acid amide of formula (1):

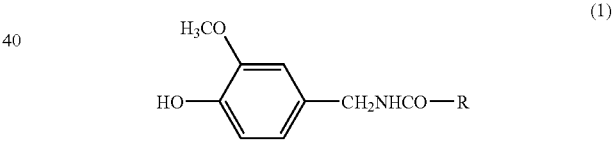

wherein —CO—R group represents a saturated or unsaturated fatty acid residue containing from 14 to 32 carbon atoms.

The present invention further provides an anti-melanoma pharmaceutical composition comprising a N-vanillyl fatty acid amide of formula (2):

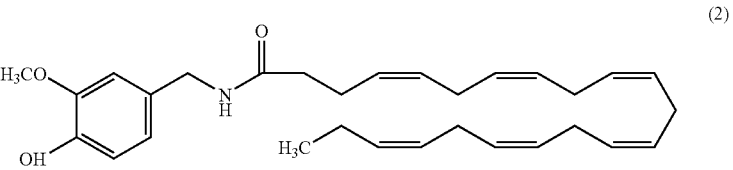

The N-vanillyl fatty acid amide is a compound produced by combining a vanillyl amide with 4,7,10,13,16,19-docosahexaenoic acid (C22:6, DHA) through an amide bond. The inventor named the amide "Dohevanil".

The present invention yet further provides a method for the treatment of tumor comprising administering a N-vanillyl fatty acid amide of formula (1):

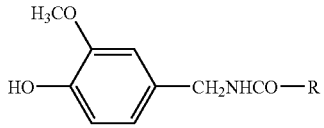

wherein —CO—R group represents a saturated or unsaturated fatty acid residue containing from 14 to 32 carbon atoms.

The present invention still further provides use of a N-vanillyl fatty acid amide of formula (1) in the manufacture of a medicament for the treatment of tumor:

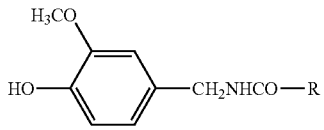

wherein —CO—R group represents a saturated or unsaturated fatty acid residue containing from 14 to 32 carbon atoms.

The term "tumor" as used herein means a malignant tumor varied from an epithelial cell or a non-epithelial cell and includes a leukemia cell derived from a hematopoietic stem cell due to the tumor growth. The term "tumor" as used herein further includes melanoma and leukemia, in particular acute leukemia.

BRIEF DESCRIPTION OF DRAWINGS

FIG. 6 is a graph showing actions of the compounds which are molecular parts of Dohevanil to B16 melanoma cells.

DETAILED DESCRIPTION OF THE INVENTION

Figure 1:
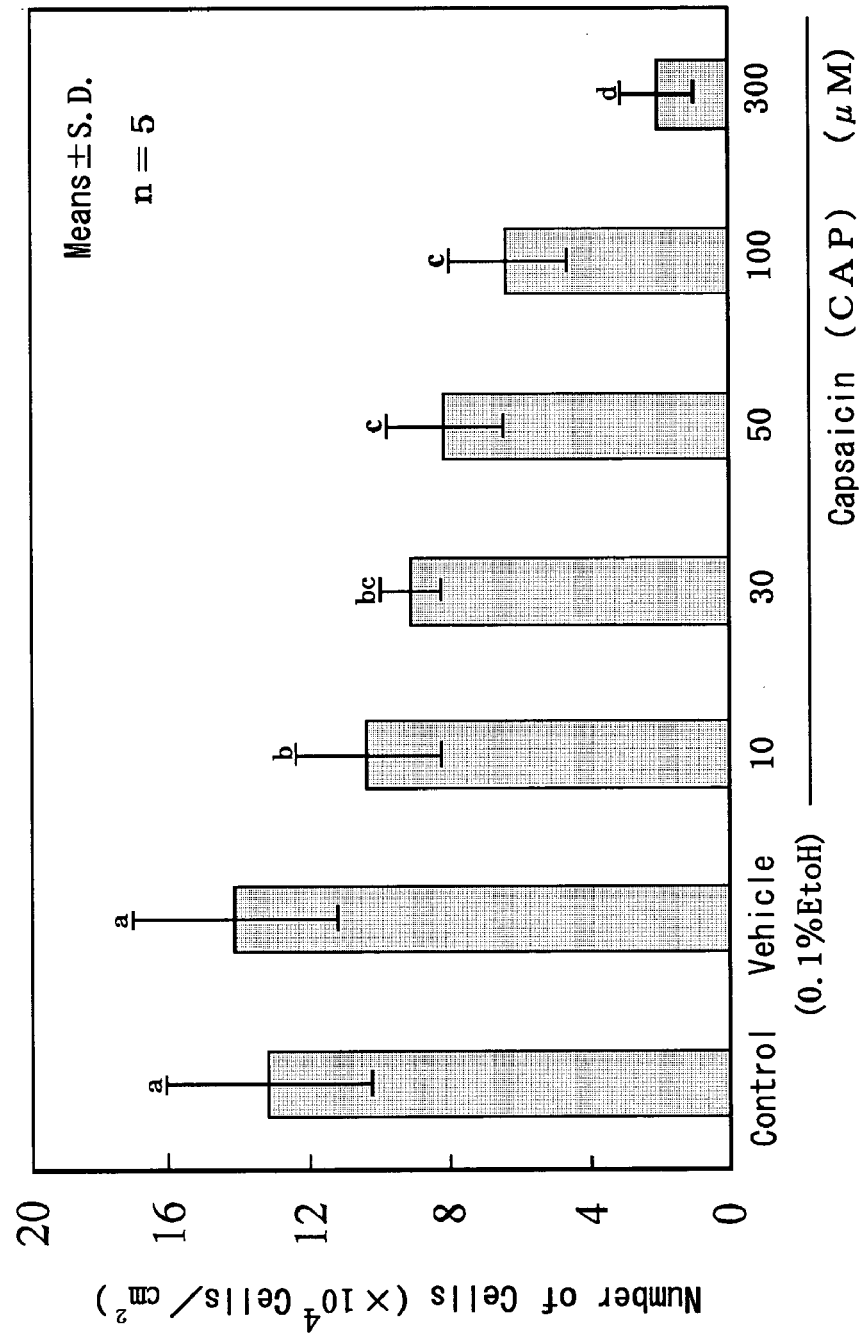
FIG. 1 is a graph showing an action of capsaicin to B16F10 melanoma cells.

A main ingredient of the anti-tumor pharmaceutical composition of the present invention "N-vanillyl fatty acid amide" is a compound produced by combining the vanillyl amine of the following formula (3) with a saturated or unsaturated fatty acid having 14 to 32 carbon atoms.

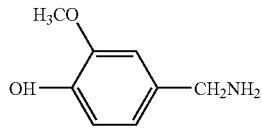

The saturated fatty acid used herein may be a straight chain saturated fatty acid or a branched chain saturated fatty acid. The straight chain saturated fatty acid includes, for example, myristic acid (C14), palmitic acid (C16), stearic acid (C18), arachic acid (C20), behenic acid (C22), lignoceric acid (C24) and cerotic acid (hexacosanoic acid) (C26), preferabley myristic acid (C14), palmitic acid (C16) and stearic acid (C18). The branched chain saturated fatty acid includes, for example, isomyristic acid (C14), isopalmitic acid (C16), isostearic acid (C18) and isoarachic acid (C20).

Preferable example of the unsaturated fatty acid includes unsaturated fatty acids having from 1 to 3 double bonds and containing 18 carbon atoms, unsaturated fatty acids having 4 or 5 double bonds and containing 20 carbon atoms and unsaturated fatty acids having 4 or more double bonds and containing 22, 24, 26, 28 or 32 carbon atoms.

Specific example of the unsaturated fatty acid includes myristic acid (C14:1), palmitoleic acid (C16:1), oleic acid (C18:1), recinoleic acid (C18:1), linoleic acid (C18:2), alpha-or gamma-linolenic acid (C18:3), eleostearic acid (C18:3), arachidonic acid (C20:4), eicosapentaenoic acid (C20:5) and 4,7,10,13,16,19-docosahexaenoic acid (C22:6). Preferable example of the unsaturated fatty acid includes oleic acid (C18:1), linoleic acid (C18:2), alpha-or gamma-linolenic acid (C18:3), eleostearic acid (C18:3), arachidonic acid (C20:4), eicosapentaenoic acid (C20:5) and 4,7,10,13,16,19-docosahexaenoic acid (C22:6, DHA).

The N-vanillyl fatty acid amides used in the present invention can be produced by a process comprising reacting a vanillyl amine chloride with a fatty acid chloride, a process comprising substituting the acyl group of capsaicin with a desired fatty acid or its ester by using a catalyzed reaction of lipase (JP-A Nos. H11-206396 or 2000-14393) or a process comprising extracting the amide from botanical or animal materials.

Where the process using a catalyzed reaction of lipase is employed, the fatty acid ester used as a crude material may include fatty acid esters having glycerin residue(s) as an alcoholic moiety such as monoester, diester, triester or mixture thereof. That is, a natural oil or fat derived from plant or animal may be used. For example, the natural oil and fat includes linseed oil, olive oil, cacao oil, corn oil, sesame oil, safflower oil, wheat germ oil, castor oil, coconut oil, peanut oil, sunflower oil, cottonseed oil, soybean oil, and shark oil.

The vanillyl amine used in the process includes a synthetic variety of the amines which are commercially available, an extracted capsaicin of red pepper and hydrolysates of other N-vanillyl fatty acid amides. The lipase used in the process includes commercially available lipase for the hydrolysis of glyceride, multi-enzyme preparations comprising a lipase as a main ingredient, a culture broth of microorganism having a lipase productivity. The enzymes may be used in the immobilized form.

The enzyme reaction should be carried out in the absence of solvent or in a hydrophobic organic solvent such as hexane, which does not inactivate the lipase. The equivalent weight ratio of the fatty acid or its ester to the vanillyl amine may be adjusted to about 30 to 1000 in order to enhance the response rate of the vanillyl amine. Optimal conditions for using the lipase such as reaction temperature and pH of aqueous phase may be determined, generally are a reaction temperature of 5 to 80 degrees Celsius and pH of 4 to 11. The produced N-vanillyl fatty acid amide may be separated from the reactant using conventional methods.

The daily dosage of the N-vanillyl fatty acid amide of the present invention varies depending on route of administration, patient's gender, symptom, age and body weight, generally ranges from about 10 to 50 mg/kg of body weight, preferably from about 20 to 30 mg/kg. The pharmaceutical composition of the present invention may comprise said N-vanillyl fatty acid amide alone as a main ingredient or in combination with other anti-tumor agent(s), desired pharmaceuticals, or suitable carrier(s).

The pharmaceutical composition of the present invention may be administered orally or parenterally. The parenteral administration includes injections such as drop infusion, hypodermic, intravenous or intramuscular injections, transdermal application with ointment or transdermal drug, and rectal application with suppository. Where the composition is administered orally, it may be prepared in the form of hard capsule, soft capsule, granule, powder, fine granule, pill, troche tablet, system of gradual active-ingredient delivery, liquid, and suspension. The preparation can be easily carried out by conventional methods in the pharmaceutical field.

Where the pharmaceutical composition of the present invention is prepared in the form of oral administration, the composition may be prepared using conventional pharmaceutical ingredients in a normal medicine such as filler, extender, binder, disintegrator, surfactant, diluents such as lubricant and excipient. Particular example of the conventional ingredients includes recipients such as milk sugar, white sugar, sodium chloride, glucose, urea, starch, calcium carbonate, kaolin, crystal cellulose and silicic acid; binders such as water, ethanol, simple syrup, glucose liquid, starch liquid, gelatin solution, carboxymethyl cellulose, shellac, methyl cellulose, potassium phosphate and polyvinyl pyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic acid monoglyceride, starch, and milk sugar; decay inhibitors such as white sugar, stearic acid, cacao butter and hydrogenated oil; absorbefacients such as quaternary ammonium salt and sodium lauryl sulfate; moisturizing agents such as glycerin and starch; absorbents such as starch, milk sugar, kaolin, bentonite and colloidal silicic acid; and lubricants such as purifed talc and stearate. If necessary, the preparation further includes colorant, preservative, perfume, flavor agent and sweetening agent.

The pharmaceutical composition of the present invention may be prepared in the form of transdermal drug delivery system such as skin embrocation to use for the treatment of tumors occurred in skin tissue, in particular melanoma. Since the N-vanillyl fatty acid amide used in the present invention have analgesia and antipruritic effects, the transdermal drug delivery system is further useful in pain and itchy relief in skin associated with tumors or other disorders.

Where the pharmaceutical composition of the present invention is prepared in the form of skin embrocation, the embrocation preferably comprises 5 wt % of the N-vanillyl fatty acid amide or more and 20 wt % of the N-vanillyl fatty acid amide or less to it.

The skin embrocation preferably includes a lower monohydric alcohol having a straight chain or branched chain alkyl group having 1 to 4 carbon atoms and may include a coating agent to enhance an adhesion to skin. Example of the coating agent includes zinc oxide, titanium oxide, aluminium oxide, magnesium oxide, zirconium oxide, magnesium carbonate, barium sulfate, hydroxyapatite, magnesium silicate, mica, kaolin, montmorillonite, bentonit, anhydrous silicic acid, zinc stearate, silicone resin, silk powder, polyethylene powder, chitin, chitosan, collagen, elastin, hyaluronic acid and cellulose alginate. If necessary, the embrocation may include surfactant and algefacient.

The present invention is further described in detail by the following examples. An object of the examples is to explain the present invention and not to limit a protective scope of the invention. The protective scope of the invention will be limited by only the claims attached to the present specification.

EXAMPLES

Example 1

Synthesis of N-vanillyl-4,7,10,13,16,19-Docosahexaenamide (Referred to as Dohevanil Herein Below)

Dohevanil was synthesized by reacting vanillyl amine with 4,7,10,13,16,19-docosahexaenoic acid (C22:6, DHA) according to the procedure described below. 1.23 g Of vanillyl amine hydrochloride (ALDRICH) was dissolved in 5 ml of tepid water at 42 degrees Celsius, 10% sodium hydroxide (2.62 ml) in an equimolar amount was added and then the mixture was stirred at 40 degrees Celsius for 20 minutes. The deposited precipitate was filtered and washed three times with cold distilled water. The filtered precipitate was dried under reduced pressure at 110 degrees Celsius for three hours and further dried under vacuum at an ambient temperature for 30 minutes to obtain 0.801 g of the vanillyl amine.

0.230 g Of the vanillyl amine and 0.591 g of 4, 7, 10, 13, 16, 19-docosahexaenic acid (DOOSAN SERDARY RESEARCH LABORATORIES) were dissolved in 13.8 ml of chloroform. Then, 0.310 g of dicyclohexylcarbodiimide (DCC) (Tokyo Kasei Kogyo Co., Ltd), 0.037 g of dimethylaminopyridine (DMAP) (Tokyo Kasei Kogyo Co., Ltd), and a very small amount of butylhydoxytoluene were added. The mixture was stirred at an ambient temperature for 42 hours. After the reaction terminated, the reaction mixture was filtered to remove the precipitate and then the filtrate was condensed to about 0.5 ml by rotary evaporator. The condensed filtrate was fractionated by silicagel column chromatography (40 g of silicagel, developing solvent: hexane/Ethyl acetate=6/4 (vol/vol)). The fraction of Dohevanil was collected, concentrated and dried to give a solid by rotary evaporator and then further dried under vacuum to give 0.311 g of colorless or citrine amorphous-like solid of Dohevanil. The obtained Dohevanil was analyzed by NMR. The result is as follows:

$^1$H-NMR (200 MHz, CDCl$_3$): δ=0.97 (3H, t, J=7.6 Hz, —C—CH$_3$), 2.1 (2H, m, Me-CH$_2$—C=C—), 2.25 (2H, m, —CH$_2$—CH$_2$—CH =CH—), 2.4 (2H, m, —CO—CH$_2$—CH=CH—), 2.83 (10H, m, —C=C —CH$_2$—C=C-×5), 3.88 (3H, S, —OCH$_3$), 4.35 (2H, d, J=2.8 Hz, —NH—CH$_2$—), 5.37 (12H, m, —CH=CH-×6), 5.6 (1H, d, J=1 Hz, —OH), 6.82 (3H, m, aromatic proton).

Example 2

Synthesis of N-Vanillylmyristamide (C14)

The substitution reaction of acyl group using a lipase, which is disclosed by JP-A-No. H11-206396, is used to synthesize N-vanillylmyristamide (C14). In the method, 37.8 mg (0.2 mmol) of vanillyl amine hydrochloride is dissolved in 10 ml of 10 mM borate buffer (pH 9.0), and then 1000 mg of Novozyme 435 (Immobilized preparation of enzyme derived from Mucor miehei:Novo Nordisk A/S), 5.80 g of methyl myristate (24 mmol) are added thereto. The mixture is reacted at 70 degrees Celsius for a given time with stirring. After the reaction, the obtained N-vanillylmyristamide is determined quantitatively. Where an amount of vanillyl amine consumed is used as a standard, the reaction yield will be about 30%, where the reaction time is 24 hours, and about 57%, where the reaction time is 72 hours.

Example 3

Synthesis of N-Vanillyloleamide (C18:1)

The synthesis is carried out in the same manner as that of example 2 except that methyl oleate is used instead of methyl myristate in the same molar number. Consequently, where an amount of vanillyl amine consumed is used as a standard, the reaction yield is about 44%, where the reaction time is 72 hours.

Example 4

Synthesis of N-Vanillyllinoleamide (C18:2)

The synthesis is carried out in the same manner as that of example 2 except that methyl linoleate is used instead of methyl myristate in the same molar number. Consequently, where an amount of vanillyl amine consumed is used as a standard, the reaction yield is about 39%, where the reaction time is 72 hours.

Example 5

Anti-Melanoma Effect of the N-Vanillyl Fatty Acid Amide Used in the Present Invention In order to examine an anti-melanoma effect of the pharmaceutical composition of the present invention, the effect of Dohevanil prepared by example 1 is compared with that of capsaicin, (1) Cells and Culture Conditions B16F10 melanoma cell used for the comparison was a malignant melanoma cell derived from a mouse. The melanoma cells were cultured under 5% $CO_2$ condition at 37 degrees Celsius in DMEM culture medium (pH7.2) including 10% of bovine fetus serum and penicillin/streptomycin solution. After the cells reached from 70% to 80% confluent, the cells were treated with trypsin-EDTA to release from the wall of culture device and were subjected to passage culture.

(2) Observation of Cytomorphology

The observation of cytomorphology was conducted using a light microscope and a fluorescence microscope.

The observation of cytomorphology using the light microscope was carried out by counting with TMS (NIKON Corporation) and photographing, after plating the cells on a multiplate, and culturing it for a given time.

The observation using the fluorescence microscope was carried out by the process comprising washing with PBS (−) a suspension of B16F10 cells treated with an agent for a given time (1×10$^6$ cells/ml), fixing the cells with 4% paraformaldehyde overnight, washing the cell fixed solution with PBS(−), suspending the cells in 20 µl of PBS (−), mixing 2 µl of fluorescence indicator (Hoechst 33342 (1 mM)) with each 5 µl of the cell suspension, placing a cover glass on the mixture, watching it using the fluorescence microscope (U region) and photographing.

(3) Measuring the Number of Cells

The number of cells were measured by the process comprising suspending the cells collected, sufficiently mixing the suspension with a trypan blue stain solution in the same volume of the suspension, watching the suspension using a phase contrast microscope and measuring the number of cells with a hemocytometer (Burker-Turk hemocytometer, Nippon Rinsho Kikai Kogyo Ltd.)

(4) Quantitative Determination of Melanin in Cells

The melanin was quantitatively determined by the process comprising collecting the cells, suspending the cells in 200 µl PBS (−), adding 1 ml of ethanol/ether mixture to the suspension, standing it for 15 minutes, centrifuging it to obtain the pellet, suspending the obtained pellet in 1 ml of 10% DMSO-1N NaOH solution, incubating the suspension at 80 degrees Celsius for 15 minutes and measuring absorbance of the supernatant at a wavelength of 475 nm. A pre-determined absorption per a given number of melanoma cells was used as a control value (100). The content of melanin in each sample was shown at the relative value.

(5) Determination of Degrees of Hotness at the Relative Value by Organoleptic Examination Relative degrees of hotness of capsaicin and Dohevanil were determined on the basis of a minimum value of hotness obtained according to the process comprising placing a droplet of each alcohol solution on a cover glass, evaporating the alcohol from the droplet and detecting the hotness with the tongue of examiner. When the degree of hotness of capsaicin was regarded as 1 (one), that of Dohevanil was evaluated as $10^{-5}$. As a result, it was found out that Dohevanil had a very low hotness and acrid.

Comparative Example

In order to examine the action of capsaicin to the growth of melanoma cells, the number of the cells were measured after 10 µM, 30 µM, 50 µM, 100 µM, or 300 µM of capsaicin was added to the MDEM media in which the melanoma cells exist and then the cells were cultured for 48 hours. As a result of the culture for 48 hours, it was observed that capsaicin suppressed the growth of the cells depending on the concentration in comparison with the control. In order to examine the action of Dohevanil to the growth of melanoma cells, the number of the cells were measured in the same manner as conducted for capsaicin except that capsaicin was replaced with Dohevanil. The melanoma cells were cultured in 10 µM, 30 µM, 50 µM, or 100 µM of Dohevanil.

Figure 2:
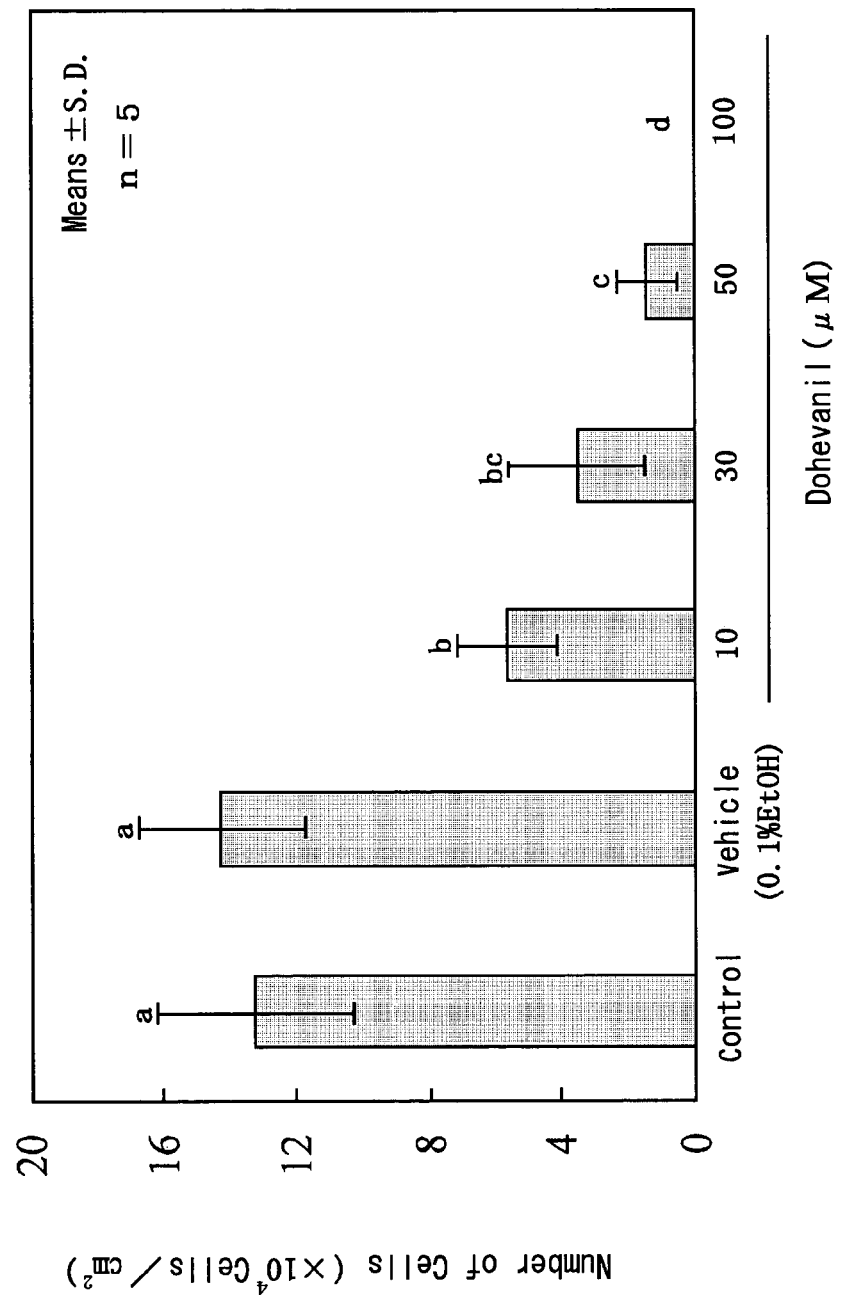
FIG. 2 is a graph showing an action of Dohevanil to B16F10 melanoma cells.

Consequently, as shown in FIGS. 1 and 2, Dohevanil suppressed the growth of the cells depending on the concentration in the same way capsaicin did. In particular, where the concentration was 50 µM, the culture with capsaicin included about 60% of the cells in the control culture, in contrast, the culture with Dohevanil included the lesser cells, about 10% of the cells in the control. Where the concentration was 100 µM, the culture with capsaicin included about 50% of the cells in the control. In contrast, that with Dohevanil included zero (0) % of the cells, that is, the survival ratio became zero. Accordingly, it is apparent that Dohevanil has the suppression effect of the growth of melanoma cells much stronger than that of capsaicin.

The shape and appearance of the melanoma cells treated in the presence of capsaicin in the concentration of 300 µM or Dohevanil in the concentration of 50 µM was observed using a phase contrast microscope. As a result, it was indicated that the melanoma cells treated with Dohevanil in the lower concentration which adhered to the wall of culture vessel was extremely reduced, and the number thereof was much lesser than the number of the melanoma cells treated with capsaicin in the higher concentration.

The shape of the cells was observed using Hoechst33342 (dye) which specifically combined with the chromosome by fluorescence microscope to find out whether or not the cell death by capsaicin or Dohevanil was due to the apoptosis. As a result, the aggregation of chromatins and the disorder of nuclear shape, which are characteristics of the cell death by apoptosis, were observed by comparison with the control in each concentration of capsaicin or Dohevanil. It is apparent from the foregoing that both of capsaicin and Dohevanil induce the apoptosis to melanoma cells, and in particular Dohevanil strongly induces the apoptosis.

As mentioned above, it has been found out that Dohevanil used in the pharmaceutical composition of the present invention is very low in hotness and stimulus, and induces the apoptosis to strongly suppress the growth of melanoma cells by comparison with capsaicin.

Example 6

Anti-Tumor Effects of the N-Vanillyl Fatty Acid Amide Used in the Present Invention In order to make a comparison between the anti-tumor effects of capsaicin and Dohevanil, the following experimentation was carried out using HeLa cells derived from human uterocervical cancer as a tumor cell and NIH/3T3 cells as a normal cell. These cells used in the experimentation were cultured in RPMI-1640 medium (pH7.2) with 5% bovine fetal serum under the culture conditions being maintained in 5% $CO_2$ and at 37 degrees Celsius. capsaicin or Dohevanil was added to each of the cell suspensions in the concentration of 10 µM, 30 µM, 50 µM, or 100 µM and then the cells were cultured. In this comparative example, the capability of cell growth was measured by WST-1 method and LDH active release into the supernatant as an indicator.

Figure 3:
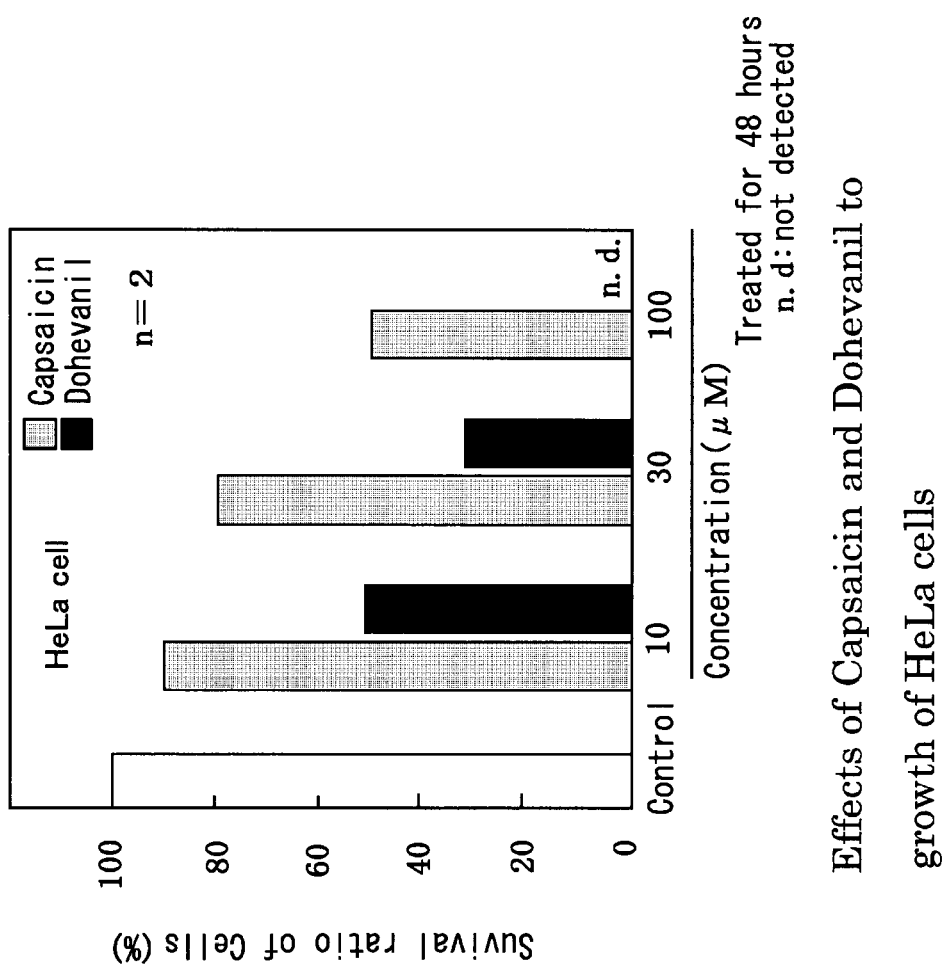
FIG. 3 is a graph showing actions of capsaicin and Dohevanil to HeLa cells.
Figure 4:
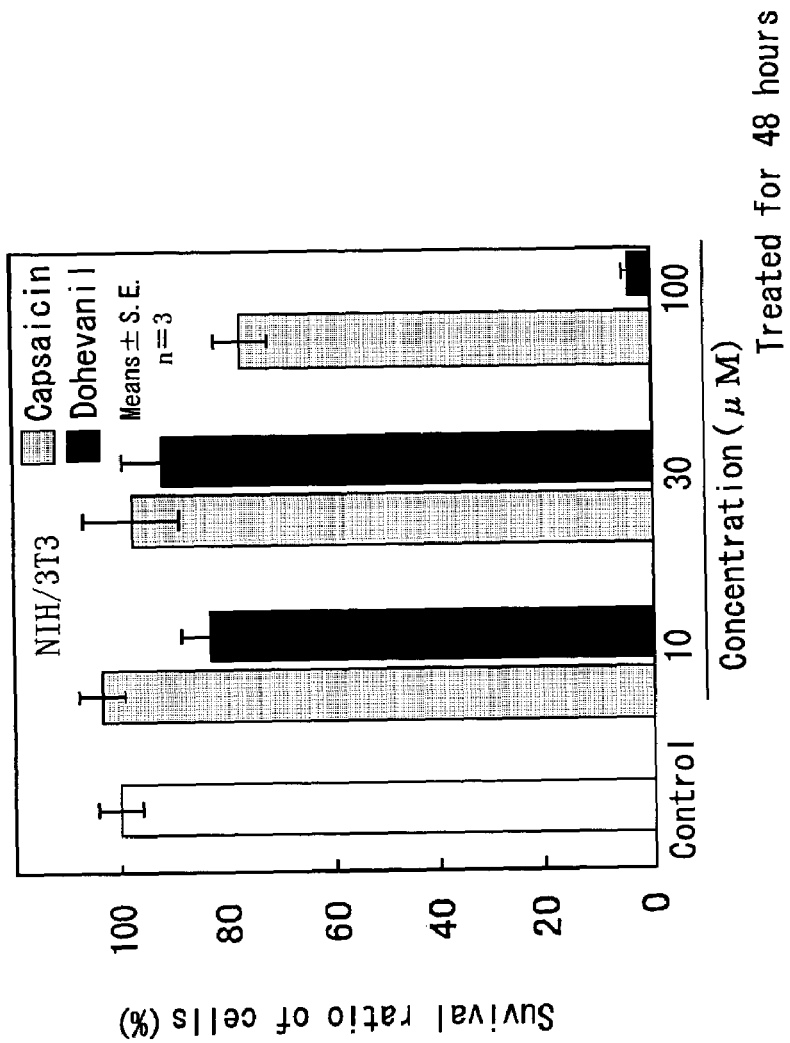
FIG. 4 is a graph showing actions of capsaicin and Dohevanil to NIH/3T3 cells.

As shown in FIG. 3, although both capsaicin and Dohevanil suppress the growth of HeLa cells depending on their concentrations, the suppression effect of Dohevanil is stronger than capsaicin. In particular, when the concentration is 100 µM, although the survival ratio of the cells with capsaicin is about 50%, that with Dohevanil is zero (0) %. While, as shown in FIG. 4, both capsaicin and Dohevanil hardly act to NIH/3T3 cells where their concentration is 30 µM or less. Accordingly, it is apparent as compared with capsaicin that Dohevanil is very low in the degree of hotness and stimulus, and coincidentally has a higher anti-tumor effect with a low action to the normal cells.

By the way, it is considered according to the measurement of caspase 3 activity that both capsaicin and Dohevanil induce the apoptosis to cause the cell death.

In this connection, the term "WST-1 method" used in the example means a method comprising reducing a formazan by using a reductase activity of mitochondria and determining an absorption of the coloring. The absorption may be used as an indicator of the cell growth because the reductase activity of mitochondria is lost if the cells die. The term "LDH active release" as used herein means that LDH (lactate dehydrogenase) is released due to a destruction of cell membrane accompanied with a cell death, and the measured value of the active release can be used as an indicator of the cell death.

Example 7

Anti-Leukemic Cell Effects of N-Vanillyl Fatty Acid Amide Used in the Present Invention In order to make a comparison between the anti-leukemic cell effects of capsaicin and Dohevanil, the following experimentation was carried out using a human acute leukemia cell U937. The U937 cells were cultured in RPMI-1640 medium (pH7.2) with 5% bovine fetal serum under the culture conditions being maintained in 5% $CO_2$ and at 37 degrees Celsius. capsaicin or Dohevanil was added to each of the cell suspensions in the concentration of 10 µM, 30 µM, 50 µM, or 100 µM and then the cells were cultured. In this comparative example, the capability of cell growth was evaluated using the measured value as an indicator obtained by a method for the cell differential staining with trypan blue.

Figure 5:
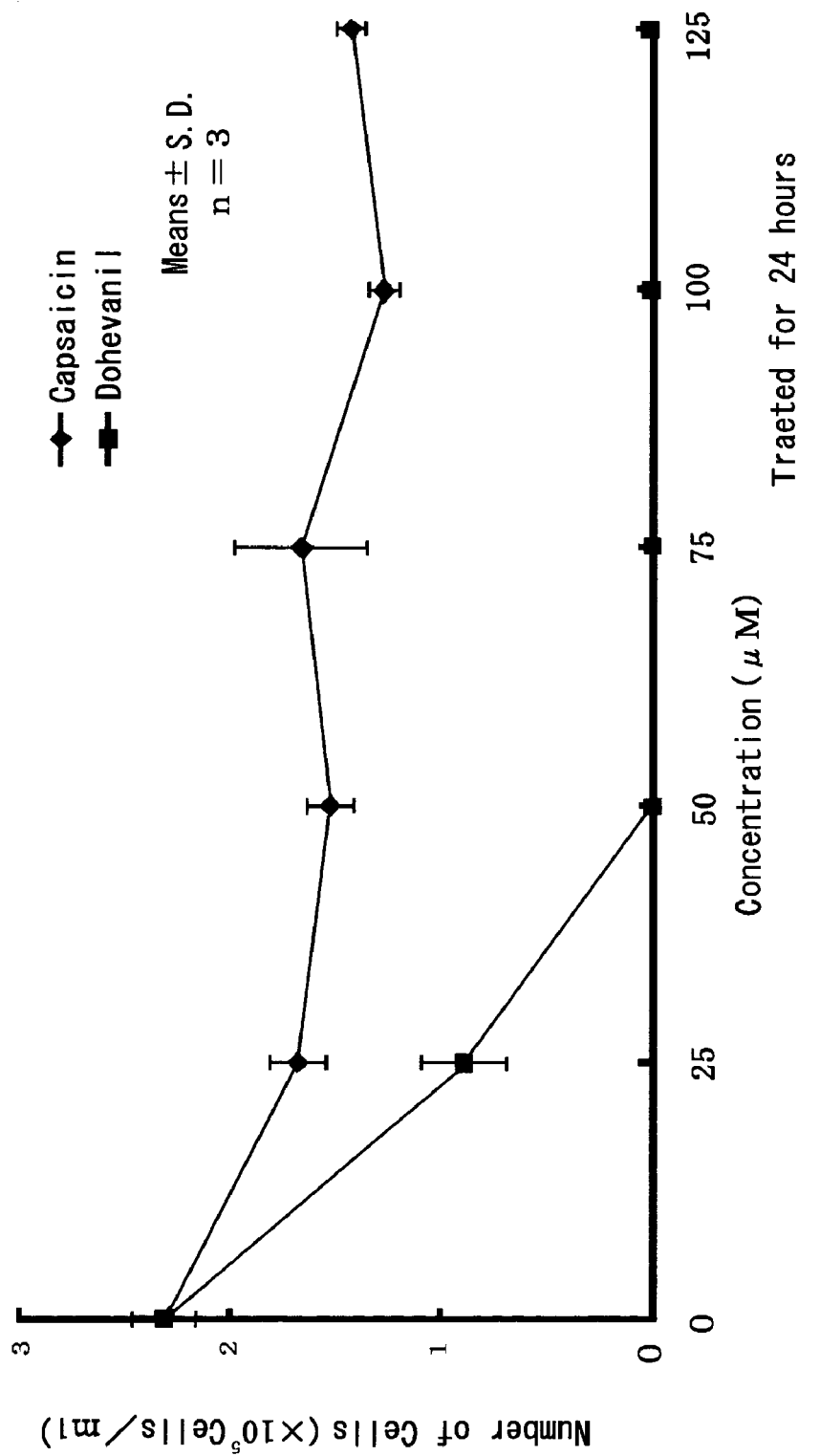
FIG. 5 is a graph showing actions of capsaicin and Dohevanil to acute leukemia cell U937.

As shown in FIG. 5, although both capsaicin and Dohevanil suppress the growth of U937 cells depending on their concentrations, the suppression effect of Dohevanil is stronger than capsaicin. In particular, when the concentration is 100 µM, although the survival ratio of the cells with capsaicin is about 50%, that with Dohevanil is zero (0) %. Accordingly, it is apparent as compared with capsaicin that Dohevanil is very low in the degree of hotness and stimulus, and coincidentally has a higher anti-leukemic cell effects. In addition, it is considered according to the measurement of caspase 3 activity that both capsaicin and Dohevanil induce the apoptosis to cause the cell death.

The method for the cell differential staining with trypan blue is a method utilizing the characters that trypan blue combines with a protein to color in blue and that trypan blue enters into the dead cells due to the loss of a membrane function to prevent from its invasion. Since the dead cells are colored in blue with trypan blue, the survival ratio of the cells can be determined by counting the stained cells using a microscope.

Example 8

Effects to B16 Melanoma Cells of Each Compound which is Used in Synthesizing Dohevanil and Contained as a Molecular Part Thereof.

In order to evaluate the effect of each of the compounds contained as a molecular part of Dohevanil to B16 melanoma cells, the cells were cultured in the same manner as that used in example 5 except that the concentration of the compound to be tested was 100 µM and the cells were treated and cultured for 48 hours. Namely, the cells were treated by adding capsaicin, Dohevanil, vanillyl amine or DHA alone to the cell culture or coincidentally adding DHA and either capsaicin or Dohevanil to the cell culture. The effects of the compounds were evaluated by making a comparison between the treatments. As shown in FIG. 6, where DHA and either capsaicin or vanillyl amine are added at the same time to treat the cells, the enhanced suppression of cell growth similar to that caused by Dohevanil was not found. Accordingly, it was not indicated that the effect of Dohevanil is a synergistic effect caused by a combination of DHA and either capsaicin or vanillyl amine.

EFFECT OF THE INVENTION

The present invention provides a pharmaceutical composition having an anti-tumor effect, in particular, an anti-melanoma effect and an anti-leukemia cell effect. In particular, the present invention provides an anti-tumor pharmaceutical composition having little side-effect to normal cells like capsaicin; having a high anti-tumor effect, in particular, an anti-melanoma effect and an anti-leukemia cell effect; and not having hotness, stimulus and proinflammatory effect.

It has been reported that capsaicin, which is a compound related to the N-vanillyl fatty acid amide of the present invention, has an anti-tumor effect both in vitro and in vivo, and both of the data obtained in vitro or in vivo are correlative (Eur J. Cancer. 1996 October; 32A(11): 1995–2003). Both of the N-vanillyl fatty acid amide of the present invention and capsaicin induce an apoptosis to suppress the growth of tumor cells, and have in common the vanillyl amine structure binding to a vaniloid receptor known as an in vivo receptor (A. Szallasi et.al., Life Sci., 47, 1399–1408 (1990)).

Taking this point into consideration, although the present specification does not state the in vivo data, it is apparent to those skilled in the art that the pharmaceutical composition will be effective in vivo.

The inevention claimed is:

1. A method for the treatment of melanoma or leukemia comprising administering to a patient in need thereof an effective amount of a N-vanillyl fatty acid amide of formula (1):

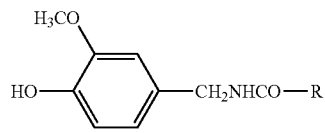

(1)

wherein —CO—R group represents a saturated or unsaturated fatty acid residue containing from 14 to 32 carbon atoms.

2. The method of claim 1, wherein the —CO—R group is a member selected from the group consisting of saturated fatty acid residues containing from 14 to 32 carbon atoms.

3. The method of claim 2, wherein the —CO—R group is a member selected from the group consisting of myristic acid residue (C14), palmitic acid residue (C016) and stearic acid residue (C18).

4. The method of claim 1, wherein the —CO—R group is a member selected from the group consisting of unsaturated fatty acid residues containing from 14 to 32 carbon atoms.

5. The method of claim 4, wherein the —CO—R group is a member selected from the group consisting of unsaturated fatty acid residues having from 1 to 3 double bonds and containing 18 carbon atoms and unsaturated (any acid residues having 4 or 5 double bonds and containing 20 carbon atoms.

6. The method of claim 5, wherein the —CO—R group is a member selected from the group consisting of oleic acid residue (C18:1), ricinoleic acid residue (C18:1), linoleic acid residue (C18:2), linolens acid residue (C18:3) and eleostearis acid residue (C18:3).

7. The method of claim 5, wherein the —CO—R group is a member selected from the group consisting of arachidonis acid residue (C20:4) and eicosapentaeaoic acid residue (C20:5).

8. The method of claim 4, wherein the —CO—R group is a member selected from the group consisting of unsaturated fatty acid residues having four or more double bonds and containing 22, 24, 26, 28 or 32 carbon atoms.

9. The method of claim 8, wherein the —CO—R group is 4,7,10,13,16,19-docosahexaenoic acid residue (C22:6).

* * * * *

UNITED STATES PATENT AND TRADEMARK OFFICE
CERTIFICATE OF CORRECTION

| | |
|---|---|
| PATENT NO. | : 7,034,058 B2 |
| APPLICATION NO. | : 10/634641 |
| DATED | : April 25, 2006 |
| INVENTOR(S) | : Takahata, Kyoya et al. |

Page 1 of 1

It is certified that error appears in the above-identified patent and that said Letters Patent is hereby corrected as shown below:

In Column 12, line 9, please delete "(C016)" and replace with -- (C16) --

Signed and Sealed this

Twenty-ninth Day of August, 2006

JON W. DUDAS
*Director of the United States Patent and Trademark Office*